United States Patent
Erkens et al.

(10) Patent No.: US 10,987,287 B2
(45) Date of Patent: Apr. 27, 2021

(54) POWDERED HAIR COLOUR WITH PERCARBONATE IN A WATER-SOLUBLE FILM

(71) Applicant: Henkel AG & Co. KGaA, Duesseldorf (DE)

(72) Inventors: Udo Erkens, Willich (DE); Torsten Lechner, Langenfeld (DE); Carsten Mathiaszyk, Essen (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 16/719,735

(22) Filed: Dec. 18, 2019

(65) Prior Publication Data

US 2020/0206098 A1  Jul. 2, 2020

(30) Foreign Application Priority Data

Dec. 28, 2018 (DE) ........................ 10 2018 133 686.1
Feb. 28, 2019 (DE) ........................ 10 2019 105 176.2

(51) Int. Cl.
| | | |
|---|---|---|
| *A61Q 5/10* | (2006.01) | |
| *A61K 8/11* | (2006.01) | |
| *A61K 8/19* | (2006.01) | |
| *A61K 8/25* | (2006.01) | |
| *A61K 8/81* | (2006.01) | |
| *A61K 8/73* | (2006.01) | |
| *A61K 8/46* | (2006.01) | |
| *A61K 8/41* | (2006.01) | |
| *A61K 8/34* | (2006.01) | |

(52) U.S. Cl.
CPC ................ *A61K 8/11* (2013.01); *A61K 8/19* (2013.01); *A61K 8/25* (2013.01); *A61K 8/347* (2013.01); *A61K 8/411* (2013.01); *A61K 8/415* (2013.01); *A61K 8/463* (2013.01); *A61K 8/731* (2013.01); *A61K 8/737* (2013.01); *A61K 8/8129* (2013.01); *A61Q 5/10* (2013.01); *A61K 2800/48* (2013.01); *A61K 2800/5922* (2013.01); *A61K 2800/87* (2013.01)

(58) Field of Classification Search
CPC . A61Q 5/10; A61K 8/411; A61K 8/22; A61K 8/415; A61K 8/19; A61K 8/41; A61K 2800/4324; A61K 8/347; A61K 8/731; A61K 8/46; A61K 2800/87; A61K 8/73; A61K 8/25; A61K 2800/48; A61K 8/0216
USPC ............................................................ 8/405
See application file for complete search history.

(56) References Cited

U.S. PATENT DOCUMENTS

2014/0082854 A1* 3/2014 Landa ................ G01N 33/4833
8/405

FOREIGN PATENT DOCUMENTS

| EP | 2361604 A1 | 8/2011 |
| EP | 3473238 A1 | 4/2019 |
| EP | 3086859 B1 | 5/2019 |
| GB | 2560214 A | 9/2018 |
| WO | 2015097101 A1 | 7/2015 |
| WO | 2018114886 A1 | 6/2018 |

* cited by examiner

*Primary Examiner* — Eisa B Elhilo
(74) *Attorney, Agent, or Firm* — Lorenz & Kopf, LLP

(57) ABSTRACT

The present disclosure pertains to the field of cosmetics and concerns a cosmetic product for changing the natural colour of keratinous fibres, in particular human hair, comprising (i) at least one package (VP) comprising a water-soluble film (F), (ii) at least one cosmetic composition (KM) which is packaged in the package (VP) and contains at least one oxidizing compound, (iii) at least one cosmetic colour composition (FZ) which is packaged in the package (VP), wherein the oxidizing compound is a solid oxidizing agent. Furthermore, the present disclosure relates to a method for colouring hair.

15 Claims, No Drawings

POWDERED HAIR COLOUR WITH PERCARBONATE IN A WATER-SOLUBLE FILM

CROSS-REFERENCE TO RELATED APPLICATION

This application claims priority to German Patent Application No. 10 2019 105 176.2, filed Feb. 28, 2019 and which claims priority to German Patent Application No. 10 2018 133 686.1, filed Dec. 28, 2018, which are both incorporated herein by reference in their entirety.

TECHNICAL FIELD

The present disclosure pertains to the field of cosmetics and relates to a cosmetic product for changing the natural colour of keratinous fibres, in particular human hair, comprising (i) at least one package (VP) comprising a water-soluble film (F), (ii) at least one cosmetic composition (KM) which is packaged in the package (VP) and contains at least one oxidizing compound, (iii) at least one cosmetic colour composition (FZ) which is packaged in the package (VP), wherein the oxidizing compound is a solid oxidizing agent. Furthermore, the present disclosure relates to a method for colouring hair.

BACKGROUND

Changing the colour of keratinous fibres, in particular hair, constitutes an important area of modern cosmetics. By employing this, the appearance of the hair as well as the latest fashion trends and also an individual's aspirations can be harmonized. In order to change the hair colour, the person skilled in the art will be aware of a variety of possibilities.

The colour of hair can be temporarily changed using direct dyes. Here, fully-formed dyes diffuse out of the colorant into the hair fibres. Colouring with direct dyes is associated with little damage to the hair; a disadvantage, however, is that the colours obtained with direct dyes do not last as long and wash out more quickly.

If the consumer wants a long-lasting colour result or a nuance which is lighter than the initial colour of the hair, then oxidative colour-changing agents are usually employed. For permanent, intensive colours with appropriate fastness, what are known as oxidative dyes are used. Colorants of this type usually contain oxidative dye precursors, what are known as developer components and coupler components, which together form the actual dyes under the influence of oxidizing agents—usually hydrogen peroxide. Oxidative dyes are exemplified by excellent, long-lasting colour results.

Lightening or bleaching of hair by itself is often carried out using oxidizing agents without the addition of oxidative dye precursors. For a medium bleaching effect, hydrogen peroxide alone is sufficient for use as the oxidizing agent; to obtain a stronger bleaching effect, a mixture of hydrogen peroxide and peroxydisulphate salts is usually employed.

Oxidative colour-changing agents are usually offered for sale in the form of two-component agents, in which two different preparations are packaged separately in two separate packages and which are only mixed together shortly before use.

The first preparation is a formulation—which is usually acidic for reasons of stability—which, for example, contains hydrogen peroxide as the oxidizing agent, in concentrations of from about 1.5 to about 12% by weight. The oxidizing agent formulation is usually in the form of an emulsion or dispersion and as a rule is in a plastic bottle (developer bottle) provided with a recloseable dispensing opening.

This oxidizing agent formulation is mixed with a second preparation prior to use. This second preparation is a formulation which is alkaline, which is often in the form of a cream or a gel, and when a change of colour is desired along with lightening, additionally contains at least one oxidative dye precursor. This second preparation may, for example, be provided in the form of a tube or in the form of a plastic or glass container.

In the case of the usual form of application described above, the second preparation, which contains the alkalizing agent and/or the oxidative dye precursors, is transferred from the tube or container into the developer bottle and then mixed with the hydrogen peroxide preparation already in the developer bottle by shaking. In this manner, the ready-to-use mixture is produced in the developer bottle. Application to the hair is then carried out via a small nozzle or dispensing opening at the top of the developer bottle. The nozzle or dispensing opening is opened after shaking and the ready-to-use mixture can be dispensed by squeezing the flexible developer bottle.

Using the developer bottle requires the user to have a certain amount of skill, and so some users prefer to produce the ready-to-use mixture in a mixing bowl and to apply it using a brush.

When producing the ready-to-use mixture in a bowl, both components—the first preparation which contains the oxidizing agent and the second preparation with the alkalizing agent and/or the oxidative dye precursors—are transferred in their entirety into a bowl or similar vessel and are then stirred in it, for example with the aid of a brush. The ready-to-use mixture is then removed from the mixing bowl using the brush. In this form of application, it is not necessary to use a bulky and expensive developer bottle, and research is still being carried out into inexpensive forms of packaging for the oxidizing agent preparation that use less material.

In this context, packaging in the form of sachets or pouches, which as a rule are prepared from plastic films or from metal films, are candidates for inexpensive forms of packaging which do not consume much material.

However, filling packages of this type with oxidizing agent preparations is fraught with problems which are caused by the reactivity of the oxidizing agent. Oxidizing agents are highly reactive substances which—independently of the storage conditions or of the possible presence of impurities which cause decomposition—can partially decompose, with the concomitant formation of oxygen (i.e. of gas).

As a rule, the interior volume of developer bottles which are known in the prior art are filled with the oxidizing agent composition to the half-way mark at most, but are usually only one-third filled. As a rule, developer bottles are produced from polyethylene. Because polyethylene is permeable to water vapour as well as to gases, no extra pressure or only a slight overpressure arises in the developer bottle. Furthermore, developer bottles are usually provided with stable, thick walls and a stable screw closure, so that the diffusion of water vapour or gases through the thickness of the walls is reduced and a small increase in pressure inside the bottle does not have any negative effects.

As a consequence, the packages are usually bulky, whereupon sustainability as regards environmental and resource considerations is compromised. An advantage would be gained if a solid could be used as the oxidizing agent. Then, oxidative dye precursors and oxidizing agents could also be provided in one container, because reacting the components necessitates mixing with water. Persulphates and percarbonates are known solid oxidizing agents for colour compositions. They are used in the form of salts. However, the use of salts is a disadvantage as regards adjusting the viscosity of the ready-to-use cosmetic composition. Polyelectrolytes are in fact often used as thickening agents, such as xanthan, for example, which loses its ability to increase viscosity with increasing salt content. If the ready-to-use hair colour composition has too low a viscosity, it is unpleasant to apply and thus is less manageable.

BRIEF SUMMARY

A cosmetic product and method for colouring keratinous fibres are providing. An exemplary cosmetic product for changing the natural colour of keratinous fibres includes (i) at least one package (VP) comprising a water-soluble film (F), (ii) at least one cosmetic composition (KM) which is packaged in the package (VP) and comprises at least one oxidizing compound, (iii) at least one cosmetic colour composition (FZ) which is packaged in the package (VP), wherein the oxidizing compound is a solid oxidizing agent and is selected from the group consisting of a percarbonate salt, a perborate salt and a percarbamide salt.

In an exemplary embodiment, a method for colouring keratinous fibres includes mixing the cosmetic product as claimed in claim 1 with water to form a mixture, applying the mixture to the keratinous fibres immediately thereafter, leaving the mixture on the keratinous fibres for from about 5 to about 60 minutes, and subsequently rinsing the keratinous fibres with water and optionally washing the keratinous fibres with a surfactant-containing cleaning agent.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

The present disclosure aims to provide hair colour formulations that can be packaged safely and compactly and which can be stored in an environmentally-friendly manner, while guaranteeing easy accessibility to the contents.

The fundamental aim of the present disclosure is achieved by employing the subject matter of claim 1. Thus, in a first aspect, the present disclosure provides a cosmetic product for changing the natural colour of keratinous fibres, in particular human hair, comprising (i) at least one package (VP) comprising a water-soluble film (F), (ii) at least one cosmetic composition (KM) which is packaged in the package (VP) and contains at least one oxidizing compound, (iii) at least one cosmetic colour composition (FZ) which is packaged in the package (VP), wherein the oxidizing compound is a solid oxidizing agent and is selected from the group including a percarbonate salt, a perborate salt and a percarbamide salt.

The term "keratinous fibres", "keratin-containing fibres" or keratin fibres" should be understood to mean fur, wool, feathers and in particular human hair. Although the agent as contemplated herein is primarily suitable for lightening and colouring keratinous fibres, in principle there is no impediment to using it in other areas.

The product as contemplated herein is a product for oxidatively changing the colour of keratinous fibres, i.e. a product which is used on the human head in order to carry out an oxidative coloration, lightening or nuancing of the hair. In this context, the term "nuancing" should be understood to mean a coloration in which the colour result is lighter than the initial colour of the hair.

The cosmetic product comprises a package as the first component (i). The term "package" as used in the context of the present disclosure should be understood to mean a package which is in the form of a sachet. A sachet (pouch) is a small package in the form of a pouch or pouch which is often used when packaging cosmetics. The capacity of the package, in particular of the sachet, may, for example, be from about 1 to about 1000 mL, preferably from about 5 to about 200 mL and particularly preferably from about 10 to about 50 mL. A double sachet is a sachet which has two separate compartments. Using a double sachet considerably simplifies handling of the cosmetic product. The cosmetic composition comprising the oxidizing agent is contained in one compartment, and the colour composition, which contains developer components and coupler components, is contained in the other compartment. Providing the cosmetic product in the form of a double sachet offers the advantage of compact storage and easier handling.

The cosmetic product as contemplated herein comprises a package (VP) as the first component (i), which comprises at least one water-soluble film (F). Because the package comprises, or consists of, a water-soluble film, the cosmetic product produced from the package and ingredients can be added to water. The film dissolves and the ingredients together with the water produce a mixture which constitutes a ready-to-use cosmetic end product.

In accordance with preferred embodiments, the package is a single compartment pouch or a dual compartment pouch. In this regard, when the cosmetic product is a dual compartment pouch, the cosmetic composition (KM) is contained in a first compartment of the dual compartment pouch and the cosmetic colour composition (FZ) is contained in a second compartment of the dual compartment pouch. Alternatively, the cosmetic composition (KM) and the cosmetic colour composition (FZ) are contained in a single compartment pouch. Because liquid hydrogen peroxide has been dispensed with, the two compositions can be stored in one sachet.

In accordance with a preferred embodiment of the present disclosure, the water-soluble film is a film based on polyvinyl alcohol PVOH, wherein the polyvinyl alcohol has a degree of deacetylation of about 85% and more, preferably of about 87% and more, most preferably of approximately 89%, and/or polyvinyl alcohol has a weight average molar mass $M_w$ of from about 70000 g/mol to about 120000 g/mol, preferably of from about 80000 g/mol to about 110000 g/mol, most preferably of from about 90000 to about 100000 g/mol, measured by GPC chromatography in water, at a polydispersity of from about 3.1 to about 4.5, preferably of from about 3.5 to about 4.1.

A variety of materials are suitable for use as film materials. In accordance with a preferred embodiment of the present disclosure, the water-soluble film comprises a water-soluble polymer comprising one or more polyvinyl alcohol polymers (PVOH polymers). As an alternative, a water-soluble polymer comprises a first PVOH polymer and a second PVOH polymer, wherein the first PVOH polymer has a lower average molecular weight $M_w$ than the second PVOH polymer and/or wherein the first PVOH polymer has a lower degree of hydrolysis than the second PVOH polymer.

Polyvinyl alcohol is a thermoplastic synthetic material which is usually produced by saponification (hydrolysis) of polyvinyl acetate (PVAC). The direct synthesis pathway, i.e. via the polymerization of vinyl alcohol, is not possible. During the hydrolysis of polyvinyl acetate, even under severe reaction conditions, hardly any acetate groups are cleaved, so that polyvinyl alcohols constitute copolymers that are said to be strong. In the context of the present disclosure, a homopolymer formed from a polyvinyl acetate which undergoes a hydrolysis is described as PVOH polymer. A copolymer which is produced by polymerization of vinyl acetate with a second monomer that differs from vinyl acetate and then by hydrolysis is described as a PVOH copolymer in the context of the present disclosure.

The properties of PVOH polymers are also determined by the molecular weight and by the degree of hydrolysis. The molecular weight of the polymers has an influence on cohesion in the solid polymer. The higher the molecular weight, the greater is the cohesion. With greater cohesion, the adhesive force upon sealing the package and the strength of the package also increases. The degree of hydrolysis gives the molar fraction of hydrolysed monomer units in the polymer with respect to the total quantity of monomer units. If the degree of hydrolysis is about 90%, then about 9 out of about 10 monomer units in the PVOH polymer have been saponified and a monomer unit constitutes a vinyl acetate unit. The degree of hydrolysis has a strong influence on the solubility of the polymers in water. By using two PVOH polymers, wherein the first PVOH polymer has a lower average molecular weight $M_w$ than the second PVOH polymer and/or wherein the first PVOH polymer has a lower degree of hydrolysis than the second PVOH polymer, then simultaneously, the strength of the package and the solubility properties of the package material can be adjusted to a specific level.

The degree of hydrolysis (or also the degree of deacetylation) may, for example, be determined by measurement of the polymer using quantitative 1H-NMR and/or 13C-NMR spectroscopy and comparison with a completely acetylated or deacetylated reference polymer or with another suitable standard.

In the preferred embodiment in which two different PVOH polymers are used, it should always be the case that the degree of hydrolysis of the first PVOH polymer is lower than that of the second PVOH polymer, i.e. if the degree of hydrolysis for the second PVOH polymer is about 87%, then the degree of hydrolysis for the first PVOH polymer is less than about 87%.

In the context of the present disclosure, the "average molecular weight $M_w$" should always be assumed to be the weight average of the molecular weight. The molecular weight is investigated by gel permeation chromatography (GPC) and compared with others. In the context of preparing samples for the determination of the molecular weight, the samples were dissolved overnight in distilled water and after routine filtration were separated on a Suprema column combination which is suitable for aqueous solvents. The eluent used was a solvent mixture based on sodium chloride and disodium hydrogen orthophosphate and chromatographed with a UV and IR detector and a column oven temperature of about 30° C.

In accordance with a preferred embodiment of the present disclosure, the water-soluble polymer comprises at least about 70% by weight, preferably at least about 80% by weight, more preferably at least about 85% by weight, most preferably at least about 95% by weight, with respect to the total weight of the package, of one or more PVOH polymers. In the context of the present disclosure, the term "package" should always be understood to mean the package without the contents. The material which forms the package includes the one or more PVOH polymers in the proportions given above. The remaining components are made up of plasticizers, melting aids or other polymeric components.

In accordance with a further preferred embodiment, the water-soluble polymer furthermore comprises a polyvinyl alcohol copolymer (PVOH copolymer) and/or a polysaccharide selected from the group including methyl cellulose, carboxymethyl cellulose, ethyl cellulose, hydroxyethyl cellulose, hydroxypropyl cellulose, hydroxypropylmethyl cellulose, dextrin and hydroxypropyl starch, wherein a water-soluble polysaccharide comprising a hydroxypropyl starch is particularly preferred. These polymers constitute the further polymeric components mentioned above which may preferably be used in addition to the PVOH polymer(s) as the material for the package.

As the second component (ii), the product as contemplated herein comprises a cosmetic composition (KM) which is packaged in the package (VP) and contains at least one oxidizing compound. Thus, the cosmetic composition (KM) contains, as the first essential ingredient of the component (ii), at least one oxidizing agent which, as contemplated herein, is a solid oxidizing agent and is selected from the group including a percarbonate salt, a perborate salt and a percarbamide salt. As contemplated herein, the solid oxidizing agent is a percarbonate salt, a perborate salt and/or a percarbamate salt. An addition compound formed from hydrogen peroxide and urea is described as a percarbamide. Preferably, a percarbonate should be understood to mean an $H_2O_2$ adduct. As an example, sodium percarbonate, which is particularly preferred, is a substance with the formula $2Na_2CO_3 \cdot 3H_2O_2$. Furthermore, a perborate, in particular sodium perborate, may be used as the solid oxidizing agent. Preferably, the salts are alkali, alkaline earth or ammonium salts.

By using a solid oxidizing agent, the oxidizing compound and the cosmetic colour composition can be stored in a container because without the addition of water, the solids will only react to a negligible extent over a long time period. The complicated way of packaging liquid hydrogen peroxide can be dispensed with.

The solid oxidizing agent constitutes a replacement for the free hydrogen peroxide that is used in the prior art in colorants. The feature is associated with the advantageous effect that the cosmetic product can be transformed into a ready-to-use composition simply by mixing with water.

The physical state "solid" is with respect to standard conditions, i.e. about 25° C. and about $10^5$ Pa, when the oxidizing agent is in an undiluted form, i.e. without a solvent or diluent. Unless stated otherwise, all details regarding the physical state, unless stated to the contrary, are with respect to these standard conditions.

The concentration of the oxidizing agent in the composition (KM) is determined on the one hand from legal requirements and on the other hand from the desired effect; preferably, from about 0.5% to about 20.0% by weight solutions in water are used. Thus, as contemplated herein, the cosmetic product contains the at least one oxidizing compound, preferably the percarbonate salt, in particular sodium percarbonate, in a total quantity of from about 6% to about 25% by weight, advantageously of from about 8% to about 18% by weight, preferably of from about 10% to about 16% by weight, with respect to the total weight of the cosmetic product. The higher the oxidizing agent content in the composition (KM), the greater is the quantity of gas produced during pro rata decomposition of the oxidizing agent. Preparations containing higher concentrations of oxidizing agent are thus far more difficult to formulate so as to be stable upon storage in a package (VP) than preparations with a lower concentration.

The product as contemplated herein is used for the purposes of oxidative coloration. To this end, the preparation (KM), which contains the oxidizing agent, is mixed with a second preparation which is packaged separately from (KIM), namely the colour composition (FZ). The ready-to-use oxidative colour-changing agent is produced in this manner. The colour composition (FZ) may contain different ingredients depending on which colour is to be obtained. If an oxidative coloration is desired, then in addition to the alkalizing agent, oxidation dye precursors are also contained in the colour composition.

The cosmetic product comprises the colour composition (FZ) as the third component (iii). In accordance with a preferred embodiment of the present disclosure, a cosmetic product is provided in which the cosmetic colour composition (FZ) contains p-toluylenediamine sulphate, hydroxyethyl-p-phenylenediamine, m-aminophenol and resorcinol, wherein preferably, the quantity of p-toluylenediamine sulphate is from about 0.1% to about 20% by weight, preferably from about 0.5% to about 5% by weight, the quantity of hydroxyethyl-p-phenylenediamine is from about 0.1% to about 20% by weight, preferably from about 0.5% to about 5% by weight, the quantity of m-aminophenol is from about 0.1% to about 10% by weight, preferably from about 0.5% to about 3% by weight, or the quantity of resorcinol is from about 0.1% to about 10% by weight, preferably from about 0.5% to about 3% by weight, respectively with respect to the total weight of the cosmetic product.

For the purposes of ease of handling of the ready-to-use cosmetic finished product, it advantageously has a specific viscosity. In this connection, a very specific combination of oxidizing agents and thickening agents has been shown to be advantageous. It has been observed that raising the viscosity by an advantageous amount when using solid oxidizing agents turns out to be particularly difficult.

Preferably, in the cosmetic product as contemplated herein, in the cosmetic composition and/or in the cosmetic colour composition, at least one thickening agent is used, wherein preferably, the at least one thickening agent is a polysaccharide, preferably a mixture of at least two different polysaccharides, preferably a mixture of an at least partially ionic polysaccharide and an essentially non-ionic polysaccharide.

More preferably, in the cosmetic product as contemplated herein, a mixture formed from a cellulose gum, a hydroxyethyl cellulose and a xanthan gum is used as the thickening agent. Surprisingly, it has been shown that the combination of the thickening agents results in easier handling of the bleaching agent. Upon mixing the bleaching agent as contemplated herein which contains the three special thickening agents with water, in the first seconds of mixing, the viscosity of the mixture remains low, so that mixing can be carried out easily and quickly. The viscosity then rises and can easily be applied to the keratinous fibres because of the higher viscosity. After the usual period which is necessary for mixing and application, a maximum viscosity is obtained. The mixture, which has by then been applied to the hair, does not drip from the hair. Because of the slow rise in the viscosity which is obtained by using the thickening agents, therefore, the advantages of the improved manageability of the bleaching agent as contemplated herein are obtained.

Preferably, the quantity of cellulose gum is from about 0.2% to about 10% by weight, more preferably from about 0.5% to about 3% by weight, the quantity of xanthan gum is from about 0.1% to about 5% by weight, more preferably from about 0.5% to about 2% by weight, and/or the quantity of hydroxyethyl cellulose is from about 0.2% to about 10% by weight, more preferably from about 0.5% to about 3% by weight, respectively with respect to the total weight of the cosmetic product.

Furthermore, the term "thickening agents" as used in the context of the present disclosure should be understood to mean compounds which can bind liquids, in particular water, and increase the viscosity of these liquids. In the context of the present disclosure, this also includes gel-forming agents which are capable of thickening liquids into compositions with a gel-like consistency or into gels. The term "gel-like cosmetic agents or gels" as used as contemplated herein should be understood to mean dimensionally stable, readily deformable disperse systems formed from at least two components, the gel-forming agent (usually a solid, colloidally disperse substance with long or highly-branched compounds) and a liquid (usually water) as the dispersing agent. In the liquid, the gel-forming agent forms a three-dimensional network, wherein the individual gel-forming compounds adhere together by employing primary and/or secondary valence bonding to various points in space.

In accordance with a preferred embodiment of the present disclosure, a cosmetic product is provided, in which the at least one thickening agent is contained in the cosmetic product in a total quantity of from about 1% to about 25% by weight, preferably of from about 2% to about 15% by weight, more preferably of from about 3% to about 8% by weight, in particular of from about 4% to about 6% by weight with respect to the total weight of the cosmetic product.

The term "xanthans" as used as contemplated herein should be understood to mean naturally occurring polysaccharides which can be obtained from sugar-containing substrates with the aid of bacteria from the genus *Xanthomonas*. Preferably, the xanthan employed as contemplated herein contains d-glucose, d-mannose, d-glucuronic acid, acetate and pyruvate in a molar ratio of 28:30:20:17:5.1-6.3, wherein the main chain includes β-1,4-bonded glucose units (also described as the cellulose chain). Particularly preferred xanthans in the context of the present disclosure have the CAS No. 11138-66-2 as well as the following structural formula:

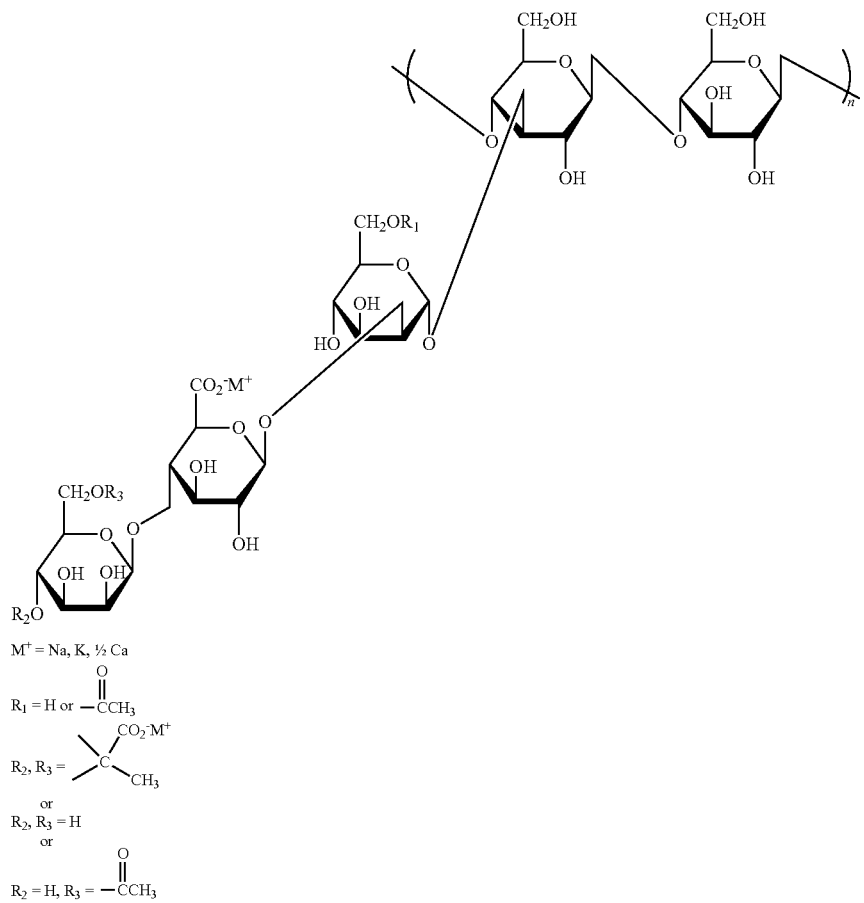

Because of its structure, xanthan constitutes a polyelectrolyte. The other special thickening agents cellulose gum (carboxymethyl cellulose) and hydroxyethyl cellulose are commercially available under the product descriptions Cekol 5000 or Tylose H 100.000 YP2. Hydroxyethyl cellulose is a cellulose ether and essentially does not contain any free acid groups.

The product as contemplated herein is used for the purposes of oxidatively changing colour. To this end, the preparation (KM) packaged in the package (VP), which preparation is the oxidizing agent preparation, is mixed with at least the one cosmetic colour composition (FZ) in order to produce the ready-to-use colour-changing agent. In order to prevent incompatibilities or in order to avoid a premature reaction, the preparations (KM) and (FZ) may be formulated separately from each other. However, this is not obligatory.

Because oxidative colouring is to be carried out with the cosmetic product as contemplated herein, the cosmetic colour composition (FZ)—hereinafter also called the preparation (FZ)—may also contain the following oxidative dye precursors. Oxidative dye precursors can be divided into developers and couplers, wherein the developers, because of their greater sensitivity as regards oxygen, are usually used in the form of their physiologically acceptable salts (for example in the form of their hydrochlorides, hydrobromides, hydrogen sulphates or sulphates). In the context of oxidative colouring, coupler components alone do not bring about any significant coloration, but always require the presence of developer components. Preferably, agents of this type contain at least one oxidative dye precursor of the developer type and at least one oxidative dye precursor of the coupler type. Particularly suitable oxidative dye precursors of the developer type are thus selected from at least one compound from the group which is formed by p-phenylenediamine, p-toluylenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, 2-methoxymethyl-p-phenylenediamine, N-(4-amino-3-methylphenyl)-N-[3-(1H-imidazol-1-yl)propyl] amine, N,N'-bis-(2-hydroxyethyl)-N,N'-bis-(4-aminophenyl)-1,3-diaminopropan-2-ol, bis-(2-hydroxy-5-aminophenyl)methane, 1,3-bis-(2,5-diaminophenoxy)propan-2-ol, N,N'-bis-(4-aminophenyl)-1,4-diazacycloheptane, 1,10-bis-(2,5-diaminophenyl)-1,4,7,10-tetraoxadecane, p-aminophenol, 4-amino-3-methylphenol, 4-amino-2-aminomethylphenol, 4-amino-2-(1,2-dihydroxyethyl)phenol, 4-amino-2-(diethylaminomethyl)phenol, 4,5-diamino-1-(2-hydroxyethyl)pyrazole, 2,4,5,6-tetraaminopyrimidine, 4-hydroxy-2,5,6-triaminopyrimidine, 2-hydroxy-4,5,6-triaminopyrimidine, 2,3-diamino-6,7-dihydro-1H,5H-pyrazolo[1,2-a]pyrazol-1-one, as well as their physiologically acceptable salts.

Particularly suitable oxidative dye precursors of the coupler type are thus selected from the group formed by 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)- amino-2-methylphenol, 2,4-dichloro-3-aminophenol, 2-aminophenol, 3-phenylenediamine, 2-(2,4-diaminophenoxy)ethanol, 1,3-bis(2,4-diaminophenoxy)propane, 1-methoxy-2-amino-4-(2-hydroxyethylamino)benzene, 1,3-bis(2,4-diaminophenyl)propane, 2,6-bis(2'-hydroxyethyl-amino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl) amino]-4,5-dimethylphenyl}amino)ethanol, 2-[3-morpholino-4-ylphenyl) amino]ethanol, 3-amino-4-(2-methoxyethoxy)-5-methylphenylamine, 1-amino-3-bis-(2-hydroxyethyl)aminobenzene, resorcinol, 2-methylresorcinol, 4-chlororesorcinol, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline, 7-hydroxyindoline or mixtures of these compounds, or their physiologically acceptable salts.

As contemplated herein, the colour composition (FZ) may contain one or more direct dyes. Suitable non-ionic direct dyes may be selected from the group formed by HC Yellow 2, HC Yellow 4, HC Yellow 5, HC Yellow 6, HC Yellow 12, HC Orange 1, Disperse Orange 3, HC Red 1, HC Red 3, HC Red 7, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, 1,4-diamino-2-nitrobenzene, 2-amino-4-nitrophenol, 1,4-bis-(2-hydroxyethyl)-amino-2-nitrobenzene, 3-nitro-4-(2-hydroxyethyl)aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenyl)amino]benzoic acid, 4-[(3-hydroxypropyl)amino]-3-nitrophenol, 4-nitro-o-phenylenediamine, 6-nitro-1,2,3,4-tetrahydroquinoxaline, 2-hydroxy-1,4-naphthoquinone, picramic acid and salts thereof, 2-amino-6-chloro-4-nitrophenol, 4-ethylamino-3-nitrobenzoic acid and 2-chloro-6-ethylamino-4-nitrophenol.

Suitable anionic direct dyes may be selected from the group formed by Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, Acid Black 52, bromophenol blue and tetrabromophenol blue.

Suitable cationic direct dyes are cationic triphenylmethane dyes such as, for example, Basic Blue 7, Basic Blue 26, Basic Violet 2 and Basic Violet 14, aromatic systems which have been substituted with a quaternary nitrogen group such as, for example, Basic Yellow 57, Basic Red 76, Basic Blue 99, Basic Brown 16 and Basic Brown 17, cationic anthraquinone dyes such as HC Blue 16 (Bluequat (B)), as well as direct dyes which contain a heterocycle containing at least one quaternary nitrogen atom, in particular Basic Yellow 87, Basic Orange 31 and Basic Red 51. The cationic direct dyes which are marketed under the trade name Arianor are also cationic direct dyes which are suitable for use in the present disclosure.

Colouring processes on keratin fibres are usually carried out in an alkaline medium. In order to care for the keratin fibres and also the skin as much as possible, however, setting the pH too high is not desirable. Thus, preferably, the pH of the preparation (FZ) is between about 7 and about 11, in particular between about 8 and about 10.5. The pHs in the context of the present disclosure are pH values which are measured at a temperature of about 22° C.

The cosmetic product may contain at least one alkalizing agent. The cosmetic product or the preparation (FZ) may contain at least one alkalizing agent. The alkalizing agents which are used as contemplated herein to set the preferred pH may be selected from the group formed by ammonia, alkanolamines, basic amino acids, as well as inorganic alkalizing agents such as alkali (alkaline earth) metal hydroxides, alkali (alkaline earth) metal metasilicates, alkali (alkaline earth) metal phosphates and alkali (alkaline earth) metal hydrogen phosphates. Preferred inorganic alkalizing agents are magnesium carbonate, sodium hydroxide, potassium hydroxide, sodium silicate and sodium metasilicate.

Particularly preferably, the cosmetic product additionally contains at least one inorganic alkalizing agent which is solid at about 20° C. and about $10^5$ Pa, among them at least one sodium silicate or sodium metasilicate with a molar $SiO_2/Na_2O$ ratio of ≥2, preferably from about 2.5 to about 3.5, in a total quantity of from about 10% to about 50% by weight, preferably from about 20% to about 40% by weight, respectively with respect to the total weight of the cosmetic product.

Organic alkalizing agents which may be used as contemplated herein are preferably selected from monoethanolamine, 2-amino-2-methylpropanol and triethanolamine. The basic amino acids which may be used as the alkalizing agent as contemplated herein are preferably selected from the group formed by arginine, lysine, ornithine and histidine, particularly preferably arginine. However, in the context of tests carried out in respect of the present disclosure, it has been shown that further preferred agents for the present disclosure additionally contain an organic alkalizing agent. One embodiment of the first aspect of the present disclosure agent additionally contains at least one alkalizing agent which is selected from the group formed by ammonia, alkanolamines and basic amino acids, in particular from ammonia, monoethanolamine and arginine or its acceptable salts.

The cosmetic product may furthermore contain additional active substances, auxiliary substances and additives. Thus, for example, it may contain one or more fatty components from the group formed by $C_{12}$-$C_{30}$ fatty alcohols, $C_{12}$-$C_{30}$ fatty acid triglycerides, $C_{12}$-$C_{30}$ fatty acid monoglycerides, $C_{12}$-$C_{30}$ fatty acid diglycerides and/or hydrocarbons.

Preferably, the cosmetic product may additionally contain a surface-active substance wherein, depending on the field of application, such surface-active substances are described as surfactants or as emulsifying agents: they are preferably selected from anionic, zwitterionic, amphoteric and non-ionic surfactants and emulsifying agents.

Preferably, the cosmetic product contains at least one anionic surfactant. Preferred anionic surfactants are fatty acids, alkyl sulphates, alkylether sulphates and ether carboxylic acids containing 10 to 20 C atoms in the alkyl group and up to 16 glycol ether groups in the molecule.

Furthermore, the cosmetic product may additionally contain at least one zwitterionic surfactant. Preferred zwitterionic surfactants are betaines, N-alkyl-N,N-dimethylammonium glycinates, N-acyl-aminopropyl-N,N-dimethylammonium glycinates, and 2-alkyl-3-carboxymethyl-3-hydroxyethyl imidazolines. A preferred zwitterionic surfactant is known by the INCI name Cocamidopropyl Betaine.

Furthermore, the cosmetic product may contain at least one amphoteric surfactant. Preferred amphoteric surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids. Particularly preferred amphoteric surfactants are N-cocoalkylaminopropionate, as cocoacylaminoethylaminopropionate, and $C_{12}$-$C_{18}$-acylsarcosine.

It has also been shown to be advantageous for the cosmetic product to contain further nonionogenic surface-active substances. Preferred non-ionic surfactants are alkylpolyglycosides as well as alkylene oxide addition products with fatty alcohols and fatty acids respectively with 2 to 30 mol of ethylene oxide per mol of fatty alcohol or fatty acid. Preparations with excellent properties are also obtained when they contain fatty acid esters of ethoxylated glycerine as the non-ionic surfactants.

The non-ionic, zwitterionic or amphoteric surfactants are used in proportions of from about 0.1% to about 45% by weight, preferably from about 1% to about 30% by weight, and more particularly preferably from about 1% to about 15% by weight with respect to the total weight of the cosmetic product.

Furthermore, the cosmetic product may contain other active substances, auxiliary substances and additives such as, for example, non-ionic polymers such as, for example, vinylpyrrolidinone/vinylacrylate copolymers, polyvinylpyrrolidinone, vinylpyrrolidinone/vinylacetate copolymers, polyethyleneglycols and polysiloxanes; additional silicones such as volatile or non-volatile, straight chain, branched or cyclic, crosslinked or non-crosslinked polyalkylsiloxanes (such as dimethicones or cyclomethicones), polyarylsiloxanes and/or polyalkylarylsiloxanes, in particular polysiloxanes containing organofunctional groups such as substituted or unsubstituted amines (amodimethicones), carboxyl-, alkoxy- and/or hydroxyl groups (dimethicone copolyols), linear polysiloxane(A)-polyoxyalkylene(B) block copolymers, grafted silicone polymers; cationic polymers such as quaternized cellulose ethers, polysiloxanes containing quaternary groups, dimethyldiallylammonium chloride polymers, acrylamide-dimethyldiallyl ammonium chloride copolymers, dimethylaminoethylmethacrylate—vinylpyrrolidinone copolymers quaternized with diethylsulphate, vinylpyrrolidinone—imidazolinium—methochloride copolymers and quaternized polyvinyl alcohol; zwitterionic and amphoteric polymers; anionic polymers such as, for example, polyacrylic acids or crosslinked polyacrylic acids; structuring agents such as glucose, maleic acid and lactic acid, hair conditioning compounds such as phospholipids, for example lecithin and cephalins; fragrancing oils, dimethylisosorbide and cyclodextrins; substances that improve the structure of fibres, in particular mono-, di- and oligosaccharides such as, for example, glucose, galactose, fructose, fruit sugar and lactose; colorants to colour the agent; antidandruff substances such as piroctone olamine, zinc omadine and climbazole; amino acids and oligopeptides; animal and/or plant-based protein hydrolysates, as well as in the form of their fatty acid condensation products or optionally anionically or cationically modified derivatives; fats and plant oils; light stabilizers and UV blockers; active substances such as panthenol, pantothenic acid, pantolactone, allantoin, pyrrolidinone carboxylic acids and their salts as well as bisabolol; polyphenols, in particular hydroxycinnamic acids, 6,7-dihydroxycoumarins, hydroxybenzoic acids, catechins, tannins, leukoanthocyanidins, anthocyanidins, flavanones, flavones and flavonols; ceramides or pseudoceramides; vitamins, provitamins and vitamin precursors; plant extracts; fats and waxes such as fatty alcohols, beeswax, montan wax and paraffins; swelling and penetrating agents such as glycerine, propylene glycol monoethyl ether, carbonates, hydrogen carbonates, guanidines, ureas as well as primary, secondary and tertiary phosphates; opacifiers such as latex, styrene/PVP and styrene/acrylamide copolymers; pearlescent agents such as ethylene glycol monostearate and distearate, as well as PEG-3-distearate, and also pigments.

The selection of these further substances will be within the purview of the person skilled in the art bearing in mind the desired properties of the cosmetic product as well as of the product as contemplated herein. Further optional components and also the quantities of those components are expressly obtainable from handbooks available to the person skilled in the art. The additional active and auxiliary substances are preferably used in the cosmetic product in respective quantities of from about 0.0001% to about 25% by weight, in particular of from about 0.0005% to about 15% by weight, respectively with respect to the total weight of the cosmetic product.

In accordance with a particularly preferred embodiment, the present disclosure concerns a cosmetic product for changing the natural colour of keratinous fibres, in particular human hair, comprising (i) at least one package (VP) comprising a water-soluble film (F) comprising a PVOH polymer, (ii) at least one cosmetic composition (KM) which is packaged in the package (VP) and contains at least one oxidizing compound and a thickening agent comprising a mixture of a cellulose gum, a hydroxyethyl cellulose and a xanthan gum, (iii) at least one cosmetic colour composition (FZ) which is packaged in the package (VP), wherein the oxidizing compound is a solid oxidizing agent and is selected from the group including a percarbonate salt, a perborate salt and a percarbamide salt and wherein the colour composition comprises p-toluylene diamine sulphate, hydroxyethyl-p-phenylenediamine, m-aminophenol and resorcinol.

The aim of the present disclosure is also achieved by employing the subject matter of claim 10. In this regard, in a second aspect, the present disclosure provides a method for colouring keratinous fibres, in particular human hair, in which a cosmetic product in accordance with the first aspect of the present disclosure is mixed with water, applied to the keratinous fibres immediately thereafter and left on the keratinous fibres for from about 5 to about 60 minutes, wherein subsequently, the keratinous fibres are rinsed with water and optionally washed out with a surfactant-containing cleaning agent, wherein preferably, the cosmetic product and water are mixed together in a mixing ratio of from about 1:1 to about 1:5, more preferably of from about 1:1 to about 1:4, and most preferably from about 1:1 to about 1:3 by weight.

Particular features of the first aspect which were only described in that context are clearly applicable as preferred features in respect of the second aspect of the present disclosure.

The following examples serve to illustrate the present disclosure without in any way limiting its scope:

EXAMPLES

For the package, films which are water-soluble were used. In particular, the products LXP9643, LXP20633 and LXP20013 from MonoSol or the product Solublon GS BTX from Aicello were used as the films.

The respective packages (VP) were filled with the following exemplary preparations (BKM) (all details as % by weight).

| Ingredients | BKM 1 | BKM 2 | BKM 3 | BKM 4 | BKM 5 | BKM 6 | BKM 7 | BKM 8 |
|---|---|---|---|---|---|---|---|---|
| Carboxymethyl cellulose (Cekol 50000) | 1.00 | 1.00 | 1.00 | 1.00 | 1.00 | 1.00 | 1.00 | 1.00 |
| Xanthan Gum (Keltrol CG-SFT) | 0.50 | 0.50 | 0.50 | 0.50 | 0.50 | 0.50 | 0.50 | 0.50 |
| Hydroxyethyl cellulose (Tylose H 100000 YP 2) | 1.00 | 1.00 | 1.00 | 1.00 | 1.00 | 1.00 | 1.00 | 1.00 |
| Sodium sulphate | 0.25 | 0.25 | 0.25 | 0.25 | 0.25 | 0.25 | 0.25 | 0.25 |
| Zinc oxide | 0.40 | 0.40 | 0.40 | 0.40 | 0.40 | 0.40 | 0.40 | 0.40 |
| Sodium metasilicate (anhydrous) | | | | | | | | 0.61 |
| Paraffinum Liquidum | | | | | 0.38 | | 0.35 | 0.22 |
| p-toluylenediaminesulphate | | | 0.33 | 0.39 | 0.15 | 0.53 | 0.37 | 2.58 |
| Hydroxyethyl-p-phenylenediamine | 1.0 | | | | | | | |
| Hydroxyethyl 4,5-diamino pyrazole sulphate, 1- | | 1.0 | | | | | 0.45 | |
| m-aminophenol | 0.04 | 0.36 | 0.03 | 0.01 | | 0.04 | 0.06 | 0.35 |
| 2,7-dihydroxynaphthalene | 0.04 | | | | | | | |
| 2-methylresorcinol | 0.09 | | 0.39 | 0.07 | | 0.02 | | |
| Resorcinol | 0.02 | | 0.04 | 0.09 | 0.27 | 0.17 | 0.04 | 0.84 |
| p-amino-o-cresol | | 0.15 | | | 0.26 | | 0.32 | |
| 2-amino-3-hydroxypyridine | | | 0.08 | 0.04 | 0.26 | 0.04 | | |
| 2-amino-3-methylphenol, 4- | | | | | 0.47 | | 0.06 | |
| 2-amino-6-chloro-4-nitrophenol | | | | | 0.24 | | | |
| 4-chlororesorcinol | 0.06 | | | | | | | |
| 2-amino-4-hydroxyethyl aminoanisole sulphate | | | | | | | 0.04 | |
| 2,4-diaminophenoxyethanol, 2HCl | | | | | | | | 1.65 |
| Sodium pet-carbonate | 12.00 | 24.00 | 23.00 | 12.00 | 20.00 | 19.00 | 16.00 | 12.00 |
| Fragrance | | | | | | | | 0.10 |
| Sodium carbonate | 1.40 | 1.40 | 1.40 | 1.40 | 1.40 | 1.40 | 1.40 | |

The cosmetic compositions BKM1 to BKM8 were respectively packed into double sachets. Next, the packages were stored for 24 weeks at 40° C. Upon mixing with water, ready-to-use colour compositions could be produced.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A cosmetic product for changing the natural colour of keratinous fibres, comprising
(i) at least one package (VP) comprising a water-soluble film (F), wherein the water-soluble film comprises a first polyvinyl alcohol polymer and a second polyvinyl alcohol polymer, wherein the first polyvinyl alcohol polymer has a lower average molecular weight $M_w$ than the second polyvinyl alcohol polymer and/or wherein the first PVOH polymer has a lower degree of hydrolysis than the second PVOH polymer,
(ii) at least one cosmetic composition (KM) which is packaged in the package (VP) and comprises at least one oxidizing compound,
(iii) at least one cosmetic colour composition (FZ) which is packaged in the package (VP),
wherein the oxidizing compound is a solid oxidizing agent and is selected from the group consisting of a percarbonate salt, a perborate salt and a percarbamide salt.

2. The cosmetic product as claimed in claim 1, wherein the package is a dual compartment pouch and the cosmetic composition (KM) is included in a first compartment of the dual compartment pouch and the cosmetic colour composition (FZ) is included in a second compartment of the dual compartment pouch, or wherein the cosmetic composition (KM) and the cosmetic colour composition (FZ) are included in a single compartment pouch.

3. The cosmetic product as claimed in claim 1, wherein the at least one oxidizing compound, is included in the cosmetic product in a total quantity of from about 6% to about 25% by weight, with respect to the total weight of the cosmetic product.

4. The cosmetic product as claimed in claim 1, wherein the cosmetic composition and/or the cosmetic colour composition comprises at least one thickening agent.

5. The cosmetic product as claimed in claim 4, wherein the at least one thickening agent is included in the cosmetic product in a total quantity of from about 1% to about 25% by weight, with respect to the total weight of the cosmetic product.

6. The cosmetic product as claimed in claim 4, wherein the at least one thickening agent is a mixture of cellulose gum, a hydroxyethyl cellulose and a xanthan gum.

7. The cosmetic product as claimed in claim 1, wherein the cosmetic colour composition (FZ) comprises p-toluylenediamine sulphate, hydroxyethyl-p-phenylenediamine, m-aminophenol and resorcinol.

8. The cosmetic product as claimed in claim 1, wherein it additionally comprises at least one inorganic alkalizing agent which is solid at about 20° C. and about $10^5$ Pa, including at least one sodium silicate or sodium metasilicate with a molar $SiO_2/Na_2O$ ratio of $\geq 2$.

9. A method for colouring keratinous fibres, the method comprising:
    mixing the cosmetic product as claimed in claim 1 with water to form a mixture,
    applying the mixture to the keratinous fibres immediately thereafter,
    leaving the mixture on the keratinous fibres for from about 5 to about 60 minutes, and
    subsequently rinsing the keratinous fibres with water and optionally washing the keratinous fibres with a surfactant-containing cleaning agent.

10. The cosmetic product as claimed in claim 1, wherein the first polyvinyl alcohol polymer has a lower average molecular weight $M_w$ than the second polyvinyl alcohol polymer.

11. The cosmetic product as claimed in claim 1, wherein the first polyvinyl alcohol polymer has a lower degree of hydrolysis than the second polyvinyl alcohol polymer.

12. The cosmetic product as claimed in claim 1, wherein the first polyvinyl alcohol polymer has a lower average molecular weight $M_w$ than the second polyvinyl alcohol polymer and wherein the first polyvinyl alcohol polymer has a lower degree of hydrolysis than the second polyvinyl alcohol polymer.

13. The cosmetic product as claimed in claim 4, wherein the cosmetic composition and/or the cosmetic colour composition comprise a mixture of an at least partially ionic polysaccharide and an essentially non-ionic polysaccharide as the at least one thickening agent.

14. The cosmetic product as claimed in claim 4, wherein the at least one thickening agent comprises a mixture of cellulose gum in an amount of from about 0.2% to about 10% by weight, of xanthan gum in an amount of from about 0.1% to about 5% by weight, and of hydroxyethyl cellulose in an amount of from about 0.2% to about 10% by weight, in each case based on the total weight of the cosmetic product, wherein the total amount of thickening agents in the cosmetic product is from about 1% to about 25% by weight, based on the total weight of the blonding agent.

15. The cosmetic product as claimed in claim 14, wherein the at least one thickening agent comprises a mixture of cellulose gum in an amount of from about 0.5% to about 3% by weight, of xanthan gum in an amount of from about 0.1% to about 5% by weight, and of hydroxyethyl cellulose in an amount of from about 0.5% to about 3% by weight, in each case based on the total weight of the cosmetic product, wherein the total amount of thickening agents in the cosmetic product is from about 4% to about 6% by weight, based on the total weight of the cosmetic product.

\* \* \* \* \*